United States Patent
Lei et al.

(10) Patent No.: US 12,338,218 B2
(45) Date of Patent: Jun. 24, 2025

(54) CRYSTAL FORM OF BENZIMIDAZOLE-2-ONE COMPOUND, SOLVATE THEREOF, CRYSTAL FORM OF SOLVATE THEREOF, AND PREPARATION METHOD THEREOF

(71) Applicant: MEDSHINE DISCOVERY INC., Jiangsu (CN)

(72) Inventors: Maoyi Lei, Shanghai (CN); Yunfu Luo, Shanghai (CN)

(73) Assignee: MEDSHINE DISCOVERY INC., Nanjing (CN)

( * ) Notice: Subject to any disclaimer, the term of this patent is extended or adjusted under 35 U.S.C. 154(b) by 768 days.

(21) Appl. No.: 17/624,462

(22) PCT Filed: Jul. 3, 2020

(86) PCT No.: PCT/CN2020/100129
§ 371 (c)(1),
(2) Date: Jan. 3, 2022

(87) PCT Pub. No.: WO2021/000934
PCT Pub. Date: Jan. 7, 2021

(65) Prior Publication Data
US 2022/0372001 A1    Nov. 24, 2022

(30) Foreign Application Priority Data
Jul. 4, 2019    (CN) .......................... 201910602489.2
May 19, 2020    (CN) .......................... 202010426911.6

(51) Int. Cl.
*C07D 235/26*    (2006.01)

(52) U.S. Cl.
CPC ........ *C07D 235/26* (2013.01); *C07B 2200/13* (2013.01)

(58) Field of Classification Search
CPC ... C07D 235/26; C07B 2200/13; Y02A 50/30; A61K 31/4184; A61P 37/00; A61P 29/00
(Continued)

(56) References Cited

FOREIGN PATENT DOCUMENTS

| EP | 3502099 A1 * | 8/2017 |
| WO | WO 2018/036470 A1 | 3/2018 |

OTHER PUBLICATIONS

Takada et al., Screening points, evaluation and control of crystal polymorphs of API form screening and selection in drug discovery stage. Pharm Stage. Jan. 15, 2007;6(10):20-25.
(Continued)

*Primary Examiner* — Taylor V Oh
(74) *Attorney, Agent, or Firm* — Mintz Levin Cohn Ferris Glovsky and Popeo, P.C.

(57) ABSTRACT

A crystal form of compound 1, a solvate thereof, a crystal form of the solvate thereof, and a preparation method therefor. Further comprised is an application of the crystal forms in the preparation of a medicament for treating diseases related to TNFα.

7 Claims, 4 Drawing Sheets

Compound 1

(58) Field of Classification Search
USPC .................................................... 548/306.4
See application file for complete search history.

(56) References Cited

OTHER PUBLICATIONS

[No Author Listed], Impurities: Guideline for Residual Solvents Q3C(R6). International Council for Harmonisation of Technical Requirements for Pharmaceuticals for Human Use. Oct. 20, 2016. 38 pages.

* cited by examiner

CRYSTAL FORM OF BENZIMIDAZOLE-2-ONE COMPOUND, SOLVATE THEREOF, CRYSTAL FORM OF SOLVATE THEREOF, AND PREPARATION METHOD THEREOF

The present application is a United States National Phase under 35 U.S.C. § 371 of International Application No. PCT/CN2020/100129, filed Jul. 3, 2020, which claims the priority of: CN201910602489.2, filed on Jul. 4, 2019; and CN202010426911.6, filed on May 19, 2020.

FIELD OF THE INVENTION

The present disclosure relates to a crystal form of compound 1, a solvate thereof, a crystal form of the solvate thereof, and a preparation method thereof. Further comprised is use of the crystal forms in the manufacture of a medicament for treating diseases related to TNFα.

BACKGROUND OF THE INVENTION

Tumor necrosis factor (TNFα) is a cytokine released mainly by mononuclear phages in response to immune stimulation. TNFα can promote most cell processes such as differentiation, recruitment, proliferation and protein degradation. TNFα has a protective effect against infectious agents, tumors and tissue damage at a low level. However, excessive release of TNFα may also cause disease. For example, when administered to mammals or humans, TNFα may cause or aggravate inflammation, fever, cardiovascular influence, bleeding, blood clotting, and acute reactions similar to acute infection and shock. The production of excessive or uncontrolled TNFα in animals or humans often indicates the following diseases: endotoxemia and/or toxic shock syndrome, cachexia, adult respiratory stress syndrome, cancer (such as solid tumors and hematological tumors), heart disease (such as congestive heart failure), viral infection, genetic disease, inflammatory disease, allergic disease, or autoimmune disease.

Cancer is a particularly devastating disease. An increase in the level of TNFα in the blood indicates the risk of cancer or the spread of cancer. Generally, carcinoma cells cannot survive in the circulatory system of a healthy subject, and one of the reasons is that the inner wall of blood vessels acts as barrier to the extravasation of carcinoma cells. Studies have shown that ELAM-1 on endothelial cells can mediate and promote colon cancer cells to adhere to endothelium treated with cytokines.

Cyclic adenosine monophosphate (cAMP) plays a role in many diseases and disorders. The increase of cAMP concentration in leukocytes during inflammation inhibits the activation of leukocytes, and then inflammatory regulatory factors including TNFα and NF-κB are released. The increase of cAMP level will also cause relaxation of the smooth muscle of the respiratory tract.

The main cellular mechanism of cAMP inactivation is the destruction of cAMP by a family of isozymes called cyclic nucleotide phosphodiesterases (PDE). It is known that there are 11 members in the PDE family. So far, it has been proved that the inhibition of PDE4 enzyme is particularly effective in inhibiting the release of inflammatory mediators and relaxing the smooth muscle of the respiratory tract. Therefore, PDE4 enzyme has become one of the popular drug targets. According to different genetic coding, the PDE-4 family can be divided into 4 subtypes (PDE-4A, B, C, D), in which the expression of PDE-4A, PDE-4B and PDE-4D in inflammatory cells (such as B cells, T cells and neutrophils, etc.) is stronger than that of PDE-4C. Inhibition of PDE4 enzyme can lead to the increase of cAMP level, thereby regulating the level of TNFα and achieving the purpose of treating diseases.

SUMMARY OF THE INVENTION

The present disclosure provides a crystal form A of compound 1, which has an X-ray powder diffraction pattern having characteristic diffraction peaks at 2θ angles of: 11.91±0.20°, 19.36±0.20°, and 23.17±0.2°.

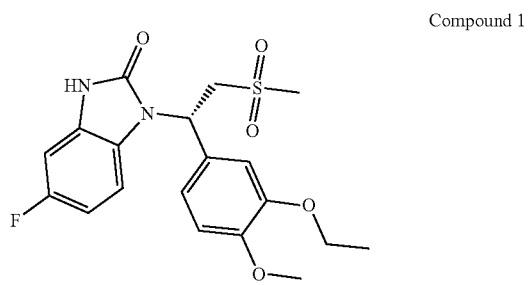

Compound 1

In some embodiments of the present disclosure, the X-ray powder diffraction pattern of the above-mentioned crystal form A of compound 1 has characteristic diffraction peaks at 2θ angles of: 11.26±0.20°, 11.91±0.20°, 12.91±0.20°, 14.27±0.20°, 19.36±0.20°, 22.26±0.20°, 23.17±0.20°, and 24.97±0.20°.

In some embodiments of the present disclosure, the X-ray powder diffraction pattern of the above-mentioned crystal form A of compound 1 has characteristic diffraction peaks at 2θ angles of: 11.26±0.20°, 11.91±0.20°, 12.91±0.20°, 14.27±0.20°, 15.83±0.20°, 17.53±0.20°, 19.36±0.20°, 20.33±0.20°, 22.26±0.20°, 23.17±0.20°, 24.97±0.20°, and 26.50±0.20°.

In some embodiments of the present disclosure, the X-ray powder diffraction pattern of the above-mentioned crystal form A of compound 1 has characteristic diffraction peaks at 2θ angles of: 11.26°, 11.91°, 12.91°, 14.27°, 15.83°, 17.53°, 19.36°, 20.33°, 22.26°, 22.59°, 23.17°, 24.97°, 26.50°, and 29.46°.

In some embodiments of the present disclosure, the analysis data of the XRPD pattern of the above-mentioned crystal form A of compound 1 are as shown in Table 1:

TABLE 1

| No. | 2θ Angle (°) | Relative intensity (%) |
|---|---|---|
| 1 | 11.26 | 51.13 |
| 2 | 11.91 | 99.15 |
| 3 | 12.91 | 51.24 |
| 4 | 14.27 | 33.57 |
| 5 | 15.83 | 28.98 |
| 6 | 17.53 | 18.87 |
| 7 | 19.36 | 100.00 |
| 8 | 20.33 | 29.34 |
| 9 | 22.26 | 48.06 |
| 10 | 22.59 | 48.31 |
| 11 | 23.17 | 72.63 |
| 12 | 24.97 | 50.67 |
| 13 | 26.50 | 22.08 |
| 14 | 29.46 | 19.25 |

In some embodiments of the present disclosure, the XRPD pattern of the above-mentioned crystal form A of compound 1 is as shown in FIG. 1.

In some embodiments of the present disclosure, the above-mentioned crystal form A of compound 1 has a differential scanning calorimetry curve having an onset of an endothermic peak at 147.0±3.0° C.

In some embodiments of the present disclosure, the DSC curve of the above-mentioned crystal form A of compound 1 is as shown in FIG. 2.

In some embodiments of the present disclosure, the above-mentioned crystal form A of compound 1 has a thermogravimetric analysis curve having a weight loss of up to 0.70% at 140.0±3.0° C.

In some embodiments of the present disclosure, the TGA curve of the above-mentioned crystal form A of compound 1 is as shown in FIG. 3.

The present disclosure also provides a solvate represented by formula (I-1)

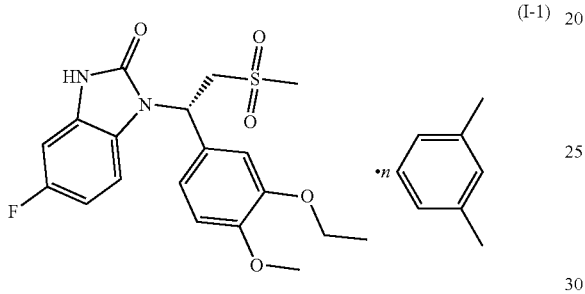

(I-1)

n is selected from 0.1~1.5.

In some embodiments of the present disclosure, in the above-mentioned solvate, n is selected from 0.1, 0.2, 0.3, 0.4, 0.5, 0.6, 0.7, 0.8, 0.9, 1, 1.1, 1.2, 1.3, 1.4, and 1.5.

In some embodiments of the present disclosure, in the above-mentioned solvate, n is 0.5.

The present disclosure also provides a crystal form B of the solvate represented by formula (I-1-1), which has an X-ray powder diffraction pattern having characteristic diffraction peaks at 2θ angles of: 6.84±0.20°, 8.90±0.20°, and 23.00±0.20°.

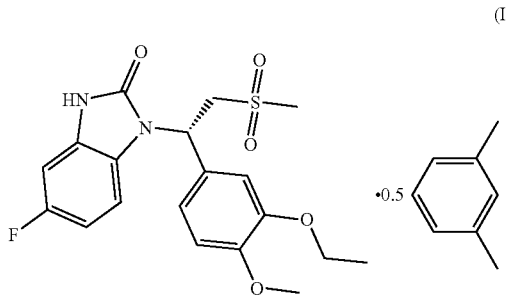

(I-1-1)

In some embodiments of the present disclosure, the above-mentioned crystal form B of the solvate has an X-ray powder diffraction pattern having characteristic diffraction peaks at 2θ angles of: 6.84±0.20°, 8.90±0.20°, 11.27±0.20°, 12.75±0.20°, 16.15±0.20°, 17.54±0.20°, 22.06±0.20°, and 23.00±0.20°.

In some embodiments of the present disclosure, the above-mentioned crystal form B of the solvate has an X-ray powder diffraction pattern having characteristic diffraction peaks at 2θ angles of: 6.84±0.20°, 8.90±0.20°, 11.27±0.20°, 12.75±0.20°, 16.15±0.20°, 17.54±0.20°, 19.17±0.20°, 19.70±0.20°, 20.41±0.20°, 22.06±0.20°, 23.00±0.20°, and 25.95±0.20°.

In some embodiments of the present disclosure, the above-mentioned crystal form B of the solvate has an X-ray powder diffraction pattern having characteristic diffraction peaks at 2θ angles of: 6.84°, 8.90°, 11.27°, 12.75°, 13.29°, 14.94°, 16.15°, 17.54°, 17.93°, 19.17°, 19.70°, 20.41°, 20.79°, 22.06°, 22.72°, 23.00°, 23.86°, 25.95°, 27.82°, 28.45°, 30.14°, and 32.87°.

In some embodiments of the present disclosure, the analysis data of the XRPD pattern of the above-mentioned crystal form B of the solvate are as shown in Table 2:

TABLE 2

| No. | 2θ Angle (°) | Relative intensity (%) |
| --- | --- | --- |
| 1 | 6.84 | 100.00 |
| 2 | 8.90 | 49.09 |
| 3 | 11.27 | 25.33 |
| 4 | 12.75 | 27.95 |
| 5 | 13.29 | 4.72 |
| 6 | 14.94 | 14.38 |
| 7 | 16.15 | 26.47 |
| 8 | 17.54 | 32.17 |
| 9 | 17.93 | 32.65 |
| 10 | 19.17 | 15.26 |
| 11 | 19.70 | 19.96 |
| 12 | 20.41 | 21.30 |
| 13 | 20.79 | 23.81 |
| 14 | 22.06 | 20.09 |
| 15 | 22.72 | 15.23 |
| 16 | 23.00 | 74.25 |
| 17 | 23.86 | 8.77 |
| 18 | 25.95 | 20.40 |
| 19 | 27.82 | 6.56 |
| 20 | 28.45 | 9.53 |
| 21 | 30.14 | 4.13 |
| 22 | 32.87 | 1.69 |

In some embodiments of the present disclosure, the XRPD pattern of the above-mentioned crystal form B of the solvate is as shown in FIG. 5.

In some embodiments of the present disclosure, the above-mentioned crystal form B of the solvate has a differential scanning calorimetry curve having an onset of an endothermic peak at 77.5±3.0° C.

In some embodiments of the present disclosure, the DSC curve of the above-mentioned crystal form B of the solvate is as shown in FIG. 6.

In some embodiments of the present disclosure, the above-mentioned crystal form B of the solvate has a thermogravimetric analysis curve having a weight loss of up to 10.46% at 80.0±3.0° C.

In some embodiments of the present disclosure, the TGA curve of the above-mentioned crystal form B of the solvate is as shown in FIG. 7.

The present disclosure also provides use of the above-mentioned crystal form A of compound 1, the above-mentioned solvate, or the crystal form B of the above-mentioned solvate in the manufacture of a medicament for treating diseases related to TNFα.

Technical Effect

The crystal form A of compound 1 disclosed herein has stable properties, low hygroscopicity, and good prospects to be made into a medicament; the compound 1 disclosed herein exhibits excellent in vitro activity of inhibiting phosphodiesterase 4B subtype (PDE4B); the compound 1 disclosed herein exhibits excellent in vitro activity of inhibiting TNFα production in hPBMC; and the compound 1 disclosed herein has a significant improvement effect on the symptoms of PMA-induced ear edema in mice in three dose groups of 0.1, 0.3 and 3 mg/ear, and can significantly inhibit ear weight gain, wherein the three dose groups all show a good dose-effect relationship.

Definition and Description

Unless otherwise specified, the following terms and phrases used herein are intended to have the following meanings. A specific term or phrase should not be considered indefinite or unclear in the absence of a particular definition, but should be understood in the conventional sense. When a trade name appears herein, it is intended to refer to the corresponding commodity or active ingredient thereof.

The intermediate compounds of the present disclosure can be prepared by a variety of synthetic methods well known to those skilled in the art, including specific embodiments listed below, embodiments formed by combining the specific embodiments listed below with other chemical synthetic methods, and equivalent alternative methods well known to those skilled in the art. The alternative embodiments include, but are not limited to, the examples of the present disclosure.

The chemical reactions in the specific embodiments disclosed herein are completed in a suitable solvent, which must be suitable for the chemical changes of the present disclosure and the reagents and materials required. In order to give the compound of the present disclosure, it is sometimes necessary for those skilled in the art to modify or select synthetic steps or reaction schemes based on the existing embodiments.

The present disclosure will be described in detail below through examples, which are not intended to limit the present disclosure in any way.

The structures of compounds disclosed herein can be confirmed by conventional methods well known to those skilled in the art. If the present disclosure relates to an absolute configuration of a compound, the absolute configuration can be confirmed by conventional techniques in the art, such as single crystal X-Ray diffraction (SXRD). In the single crystal X-Ray diffraction (SXRD), the diffraction intensity data of the cultivated single crystal is collected using a Bruker D8 venture diffractometer with a light source of CuKα radiation in a scanning mode of φ/ω scan; after collecting the relevant data, the crystal structure is further analyzed by the direct method (Shelxs97) to confirm the absolute configuration.

All solvents used in the present disclosure are commercially available and can be used without further purification.

Compounds are named according to conventional naming principles in the art or using ChemDraw® software, and commercially available compounds are named according to names in supplier catalog.

X-Ray Powder Diffractometer, XRPD Method

Instrument model: Bruker D8 advance X-ray diffractometer

Test method: About 10 to 20 mg of sample was used for XRPD detection.

Detailed XRPD parameters were as follows:
Light tube: Cu, kα, (λ=1.54056 Å).
Tube voltage: 40 kV, tube current: 40 mA
Scattering slit: 0.60 mm
Detector slit: 10.50 mm
Anti-scatter slit: 7.10 mm
Scan range: 4-40 deg
Step size: 0.02 deg
Step length: 0.12 seconds
Rotation speed of sample disk: 15 rpm Method for Determining Content Disclosed Herein Instrument model: Agilent 1260 high performance liquid chromatograph Detailed parameters of chromatographic conditions were as follows:

Column: ACE Excel 3 super C18 (4.6*150 mm id), P.N.: EXL-1111-1546U
Column temperature: 35° C.
Flow rate: 0.8 mL/min
Detection wavelength: 230 nm
Injection volume: 5 μL
Running time: 15 min
Mobile phase A: 0.04% aqueous trifluoroacetic acid solution (V/V)
Mobile phase B: 100% acetonitrile
Diluent: acetonitrile: pure water=50:50 (V/V)
Probe Wash: acetonitrile: pure water=50:50 (V/V)
Gradient elution program:

| Time (min) | Mobile Phase A (%) | Mobile Phase B (%) |
|---|---|---|
| 0.00 | 60 | 40 |
| 15.00 | 60 | 40 |

DETAILED DESCRIPTION OF THE INVENTION

Figure 1:
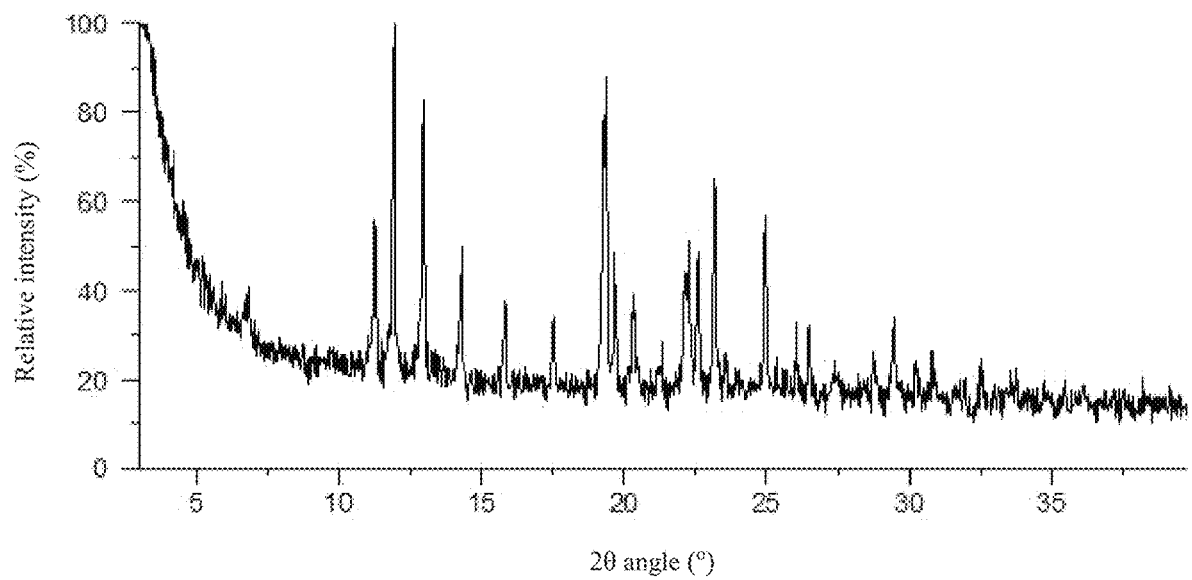
FIG. 1 is an XRPD pattern of the crystal form A of compound 1 with Cu-Kα radiation.
Figure 2:
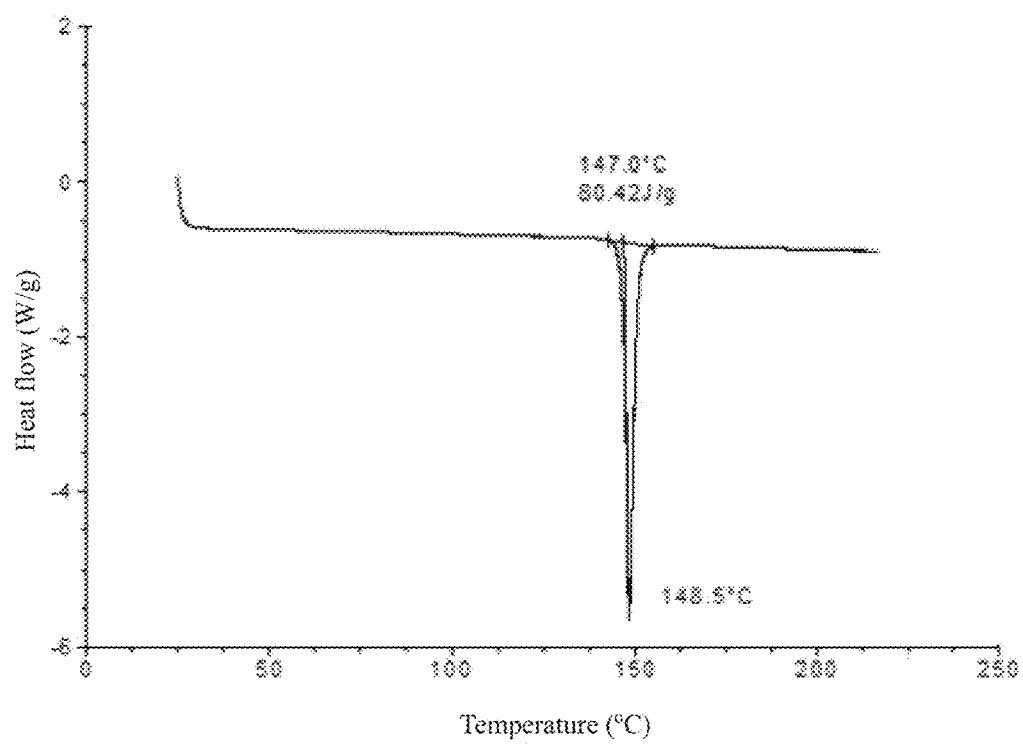
FIG. 2 is a DSC curve of the crystal form A of compound 1.
Figure 3:
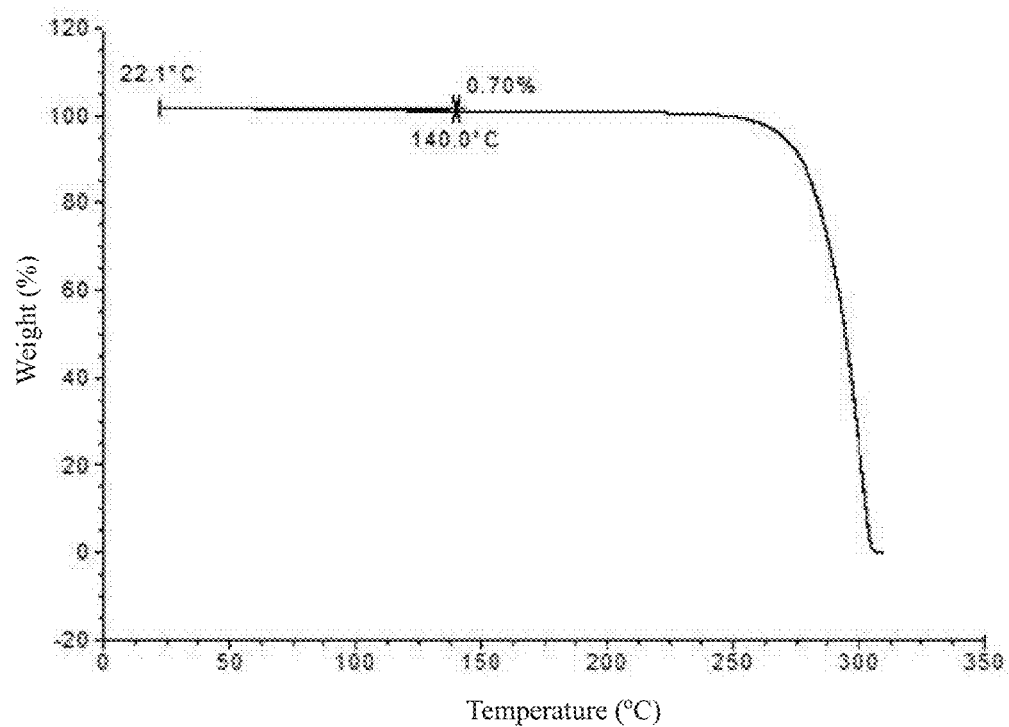
FIG. 3 is a TGA curve of the crystal form A of compound 1.

In order to better understand the content of the present disclosure, the present disclosure is further illustrated below in conjunction with specific examples, but the specific examples are not intended to limit the content of the present disclosure.

Example 1: Preparation of Amorphous Form of Compound 1

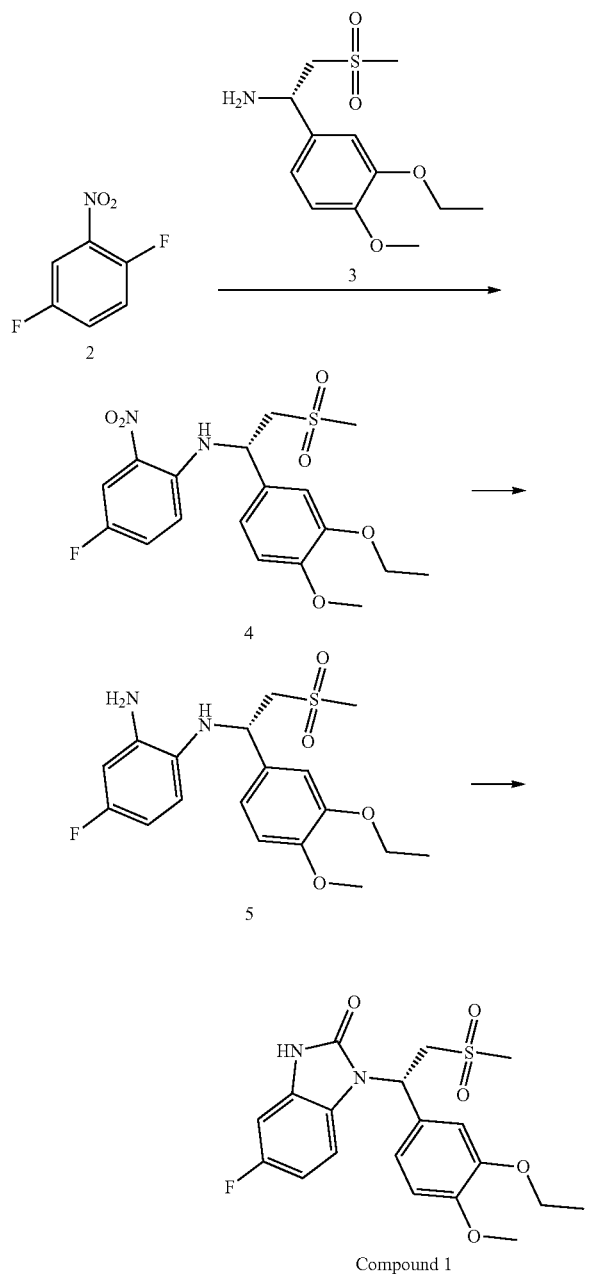

Step 1: Synthesis of Compound 4

Compound 2 (15.00 g, 94.29 mmol) was dissolved in N,N-dimethylformamide (150 mL) at room temperature under nitrogen atmosphere, and compound 3 (25.77 g, 94.29 mmol) and potassium carbonate (19.55 g, 141.43 mmol) were then added in sequence. The reaction mixture was heated to 70° C. and reacted with stirring for 16 hours. After the reaction was completed, the mixture was cooled to room temperature. Saturated brine (400 mL) was added, and the mixture was extracted with ethyl acetate (200 mL×3). The organic phases were combined, washed with saturated brine (200 mL×3), dried over anhydrous sodium sulfate, and filtered. The filtrate was concentrated under reduced pressure to remove the solvent. The resulting residue was purified by column chromatography (eluent: ethyl acetate/petroleum ether=0:1 to 2:3, volume ratio) to give the title compound 4. $^1$HNMR (400 MHz, CDCl$_3$) δ: 8.52 (d, J=6.5 Hz, 1H), 7.90 (dd, J=8.9, 3.0 Hz, 1H), 7.20-7.15 (m, 1H), 6.96-6.93 (m, 1H), 6.90-6.85 (m, 2H), 6.82-6.78 (m, 1H), 5.20-5.15 (m, 1H), 4.09-4.01 (m, 2H), 3.86 (s, 3H), 3.65 (dd, J=14.7, 8.1 Hz, 1H), 3.48 (dd, J=14.7, 4.8 Hz, 1H), 2.80 (s, 3H), 1.45 (t, J=6.9 Hz, 3H).

Step 2: Synthesis of Compound 5

Compound 4 (16.00 g, 38.79 mmol) was dissolved in a mixed solvent of ethanol (128 mL) and ethyl acetate (32 mL) at room temperature under nitrogen atmosphere, and wet palladium on carbon (5.00 g, purity: 10%) was then added. The atmosphere was replaced 3 times with hydrogen gas, and the reaction mixture was stirred to react at room temperature under hydrogen atmosphere (30 psi) for 16 hours. After the reaction was completed, the reaction mixture was filtered, and the filter cake was washed with ethyl acetate (100 mL×3). The filtrate was concentrated under reduced pressure to remove the solvent. The resulting residue was purified by column chromatography (eluent: ethyl acetate/petroleum ether=0:1 to 3:2, volume ratio) to give the title compound 5. $^1$H NMR (400 MHz, DMSO-d$_6$) δ: 7.07 (d, J=1.2 Hz, 1H), 6.91-6.84 (m, 2H), 6.36 (dd, J=10.8, 2.9 Hz, 1H), 6.30 (dd, J=8.6, 5.8 Hz, 1H), 6.09 (td, J=8.6, 2.9, 1H), 4.99 (s, 2H), 4.96 (d, J=9.3 Hz, 1H), 4.74 (td, J=9.4, 3.8 Hz, 1H), 4.02-3.96 (m, 2H), 3.73-3.67 (m, 4H), 3.39-3.36 (m, 1H), 3.01 (s, 3H), 1.30 (t, J=7.0 Hz, 3H).

Step 3: Synthesis of Amorphous Form of Compound 1

Compound 5 (12.2 g, 31.90 mmol) was dissolved in ethyl acetate (120 mL) at room temperature, and carbonyldiimidazole (15.52 g, 95.70 mmol) was then added. The reaction mixture was stirred to react at room temperature for 16 hours. After the reaction was completed, the reaction mixture was cooled to room temperature, and 1 M diluted hydrochloric acid (5 mL) and water (50 mL) were added. The mixture was extracted with ethyl acetate (80 mL×3). The organic phases were combined, washed with saturated brine (50 mL×2), dried over anhydrous sodium sulfate, and filtered. The filtrate was concentrated under reduced pressure to remove the solvent. The resulting residue was isolated by column chromatography (eluent: ethyl acetate/petroleum ether=0:1 to 3:2, volume ratio), purified by preparative HPLC (mobile phase: acetonitrile/water, neutral system), and then lyophilized in vacuum to give the title compound 1, which is amorphous. MS-ESI m/z: 409.0 [M+H]$^+$; $^1$H NMR (400 MHz, CD$_3$OD) δ: 7.11-7.08 (m, 2H), 7.06-7.04 (m, 1H), 6.93 (d, J=8.4 Hz, 1H), 6.83 (dd, J=8.5, 2.4 Hz, 1H), 6.79-6.74 (m, 1H), 6.00 (dd, J=10.5, 3.9 Hz, 1H), 4.58 (dd, J=14.8, 10.8 Hz, 1H), 4.08-3.96 (m, 3H), 3.80 (s, 3H), 2.94 (s, 3H), 1.35 (t, J=7.0 Hz, 3H).

Example 2: Preparation of Crystal Form a of Compound 1

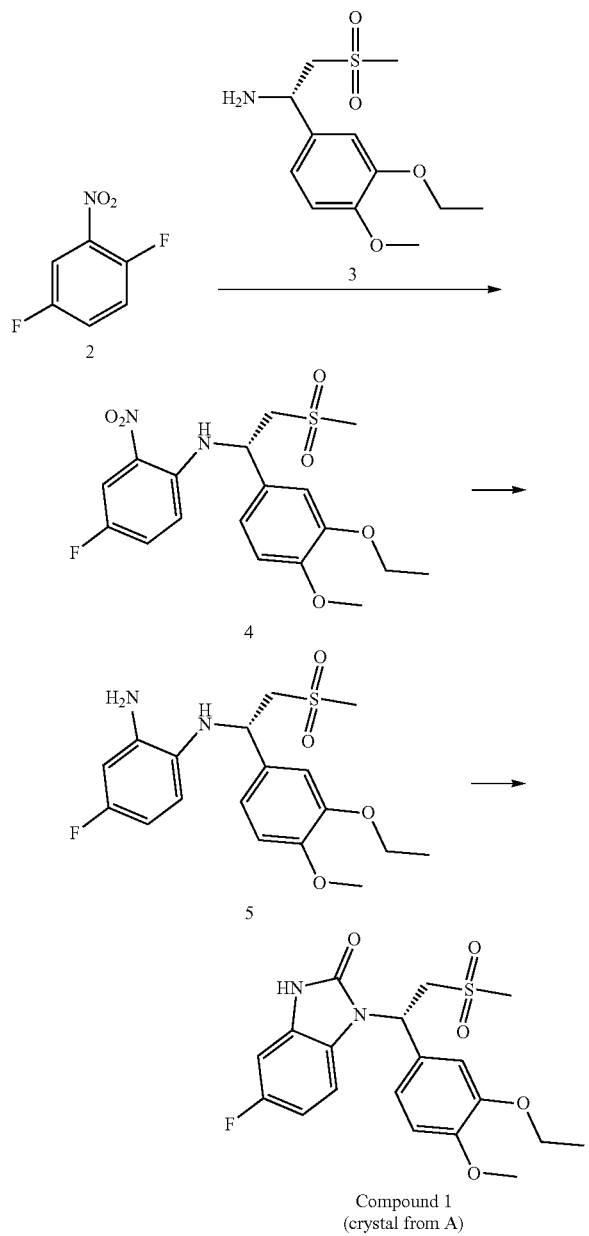

Step 1: Synthesis of Compound 4

Compound 2 (200.05 g, 1.26 mol) was dissolved in N,N-dimethylacetamide (2000 mL) at 20° C.-30° C., and then compound 3 (516.45 g, 1.89 moL) was added. Diisopropylethylamine (325.00 g, 2.52 mol) was slowly added dropwise to the above solution (over a period of about 20 minutes). After the addition was completed, the reaction mixture was heated to 110° C.-120° C. and stirred to react at 110° C.-120° C. for 16 hours. After the reaction was completed, the reaction solution was cooled to 15° C., and then slowly poured into an ice water (10500 mL). A large amount of solids precipitate out. The mixture was filtered, and the filter cake was washed with ethanol (200 mL). The filter cake was collected and the solvent was removed under reduced pressure. Sample was added to ethanol (1500 mL), and the mixture was slurried with stirring at 15° C. for 16 hours. The slurry was filtered, and the filter cake was washed with ethanol (200 mL). The filter cake was dried under reduced pressure to remove the solvent to give the title compound 4. $^1$HNMR (400 MHz, CDCl$_3$) δ: 8.52 (d, J=6.5 Hz, 1H), 7.90 (dd, J=8.9, 3.0 Hz, 1H), 7.20-7.15 (m, 1H), 6.96-6.93 (m, 1H), 6.90-6.85 (m, 2H), 6.82-6.78 (m, 1H), 5.20-5.15 (m, 1H), 4.09-4.01 (m, 2H), 3.86 (s, 3H), 3.65 (dd, J=14.7, 8.1 Hz, 1H), 3.48 (dd, J=14.7, 4.8 Hz, 1H), 2.80 (s, 3H), 1.45 (t, J=6.9 Hz, 3H).

Step 2: Synthesis of Compound 5

Compound 4 (122.83 g, 0.30 mol) was dissolved in a mixed solvent of dichloromethane (500 mL) and ethyl acetate (500 mL) at 20° C.-25° C. under nitrogen atmosphere, and wet palladium on carbon (7.50 g, purity: 10%) was then added. The atmosphere was replaced 3 times with hydrogen gas, and the reaction mixture was stirred to react at 25° C.-35° C. under hydrogen atmosphere (25-35 psi) for 16 hours (Four batches of raw materials were reacted in parallel and processed in combination). After the reaction was completed, four batches of reaction solution were combined, and filtered through Celite. The filter cake was washed with dichloromethane (200 mL). The filtrate was rotary-evaporated to dryness under reduced pressure to give a crude product. The crude product was added to ethanol (3200 mL), and the mixture was heated to 78° C. and stirred at 78° C. for 1 hour (until the reaction mixture became completely clear). The heating was stopped, and the mixture was allowed to slowly cool to 20° C. with stirring. The mixture was stirred at 20° C. for another 12 hours. During the stirring, a large amount of solids precipitated out. The reaction mixture was filtered, and the filter cake was washed with ethanol (200 mL). The filter cake was collected, and rotary-evaporated to dryness under reduced pressure to give a product (406.15 g). 329.50 g of the product was weighed and dissolved in dichloromethane (2000 mL). The mixture was purified by column chromatography (eluent: dichloromethane/methanol=1:0, volume ratio) to give compound 5. $^1$H NMR (400 MHz, DMSO-d$_6$) δ: 7.07 (d, J=1.2 Hz, 1H), 6.91-6.84 (m, 2H), 6.36 (dd, J=10.8, 2.9 Hz, 1H), 6.30 (dd, J=8.6, 5.8 Hz, 1H), 6.09 (td, J=8.6, 2.9, 1H), 4.99 (s, 2H), 4.96 (d, J=9.3 Hz, 1H), 4.74 (td, J=9.4, 3.8 Hz, 1H), 4.02-3.96 (m, 2H), 3.73-3.67 (m, 4H), 3.39-3.36 (m, 1H), 3.01 (s, 3H), 1.30 (t, J=7.0 Hz, 3H).

Step 3: Synthesis of Crystal Form A of Compound 1

Compound 5 (175.09 g, 0.46 mol) was dissolved in acetone (1800 mL) at 20° C. under nitrogen atmospheres, and then carbonyldiimidazole (163.32 g, 1.01 mol) was added. The reaction mixture was stirred to react at 15° C.-25° C. for 16 hours. After the completion of the reaction, the reaction mixture was directly concentrated under reduced pressure, and the resulting residue was dissolved in ethyl acetate (1000 mL). The mixture was washed with 1 M diluted hydrochloric acid (1000 mL×2), water (1000 mL×2), and then saturated brine (1000 mL). The organic phase was dried with anhydrous sodium sulfate, and filtered, and the filtrate was concentrated under reduced pressure to remove the solvent. The resulting residue was added to ethanol (360 mL), stirred for 30 minutes, and then filtered. The filter cake was washed with ethanol (100 mL). The filter cake was collected, and the solvent was removed under reduced pressure to give a product. After the product was obtained, the product was added to a mixed solvent of ethanol (150 mL) and ethyl acetate (150 mL). The reaction mixture was heated to 78° C. and stirred at 78° C. until the reaction solution became clear. The heating was stopped, and the reaction solution was allowed to naturally cool to 20° C. with stirring. The stirring was continued for another 12 hours. Solids precipitated out during the stirring. The mixture was filtered, and the filter cake was washed with ethanol (50 mL×2). The filter cake was collected, and the solvent was removed under reduced pressure to give a product. After the product was obtained, the product was added to a mixed solvent of ethanol (60 mL) and ethyl acetate (60 mL). The reaction mixture was stirred at 20° C. for 2 hours, and then filtered. The filter cake was washed with ethanol (10 mL). The filter cake was collected, and the solvent was removed under reduced pressure. The filter cake was then dried in vacuum for 6 hours (temperature: 40-45° C., pressure: —0.08 MPa) to give the title crystal form A of compound 1. MS-ESI m/z: 409.0 [M+H]$^+$; $^1$H NMR (400 MHz, CD$_3$OD) δ: 7.11-7.08 (m, 2H), 7.06-7.04 (m, 1H), 6.93 (d, J=8.4 Hz, 1H), 6.83 (dd, J=8.5, 2.4 Hz, 1H), 6.79-6.74 (m, 1H), 6.00 (dd, J=10.5, 3.9 Hz, 1H), 4.58 (dd, J=14.8, 10.8 Hz, 1H), 4.08-3.96 (m, 3H), 3.80 (s, 3H), 2.94 (s, 3H), 1.35 (t, J=7.0 Hz, 3H).

Example 3: Preparation of Crystal Form A of Compound 1

About 175 mg of amorphous compound 1 was added to 1.0 ml of ethanol, and dissolved with ultrasound. The mixture was further subjected to ultrasound, and a large amount of white solid precipitated out. The suspension was stirred at room temperature for 3 hours, and then centrifuged to give a solid, which was the crystal form A of compound 1.

Example 4: Preparation of Crystal Form B of the Solvate of Compound 1

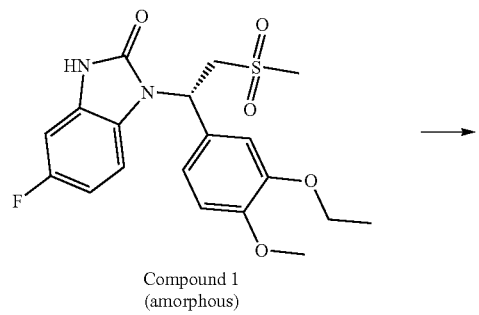

Compound 1
(amorphous)

→

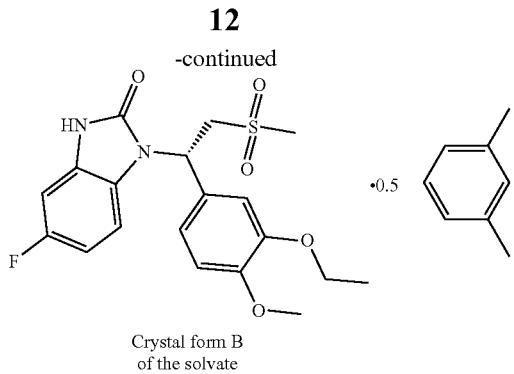

Crystal form B
of the solvate

About 24 mg of amorphous compound 1 was added to 0.2 ml of m-xylene, and the suspension was stirred at room temperature for about 2 days. The mixture was separated by centrifugation to give a solid, which was the crystal form B. $^1$H NMR (400 MHz, CDCl$_3$) δ: 8.21 (s, 1H), 7.15 (dd, J=7.4, 7.4 Hz, 0.5H), 7.03 (dd, J=2.3 Hz, 1H), 7.02 (dd, J=8.3, 2.3 Hz, 1H), 7.00-6.97 (m, 2.5H), 6.84-6.78 (m, 3H), 5.76 (dd, J=9.5, 4.2 Hz, 1H), 4.71 (dd, J=14.8, 9.5 Hz, 1H), 4.06 (q, J=7.0 Hz, 2H), 3.84 (dd, J=15.1, 4.8 Hz, 1H), 3.84 (s, 3H), 2.78 (s, 3H), 2.32 (s, 3H), 1.44 (t, J=7.0 Hz, 3H).

Assay Example 1: Study on the Hygroscopicity of Crystal Form a of Compound 1

Figure 4:
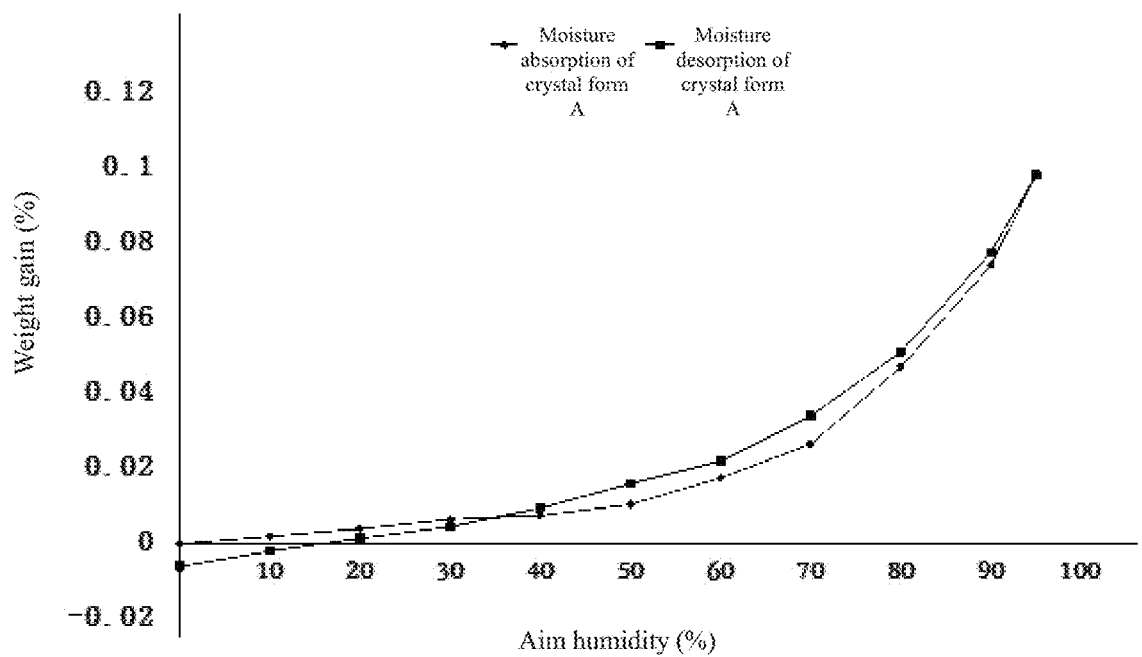
FIG. 4 is a DVS curve of the crystal form A of compound 1.
Figure 5:
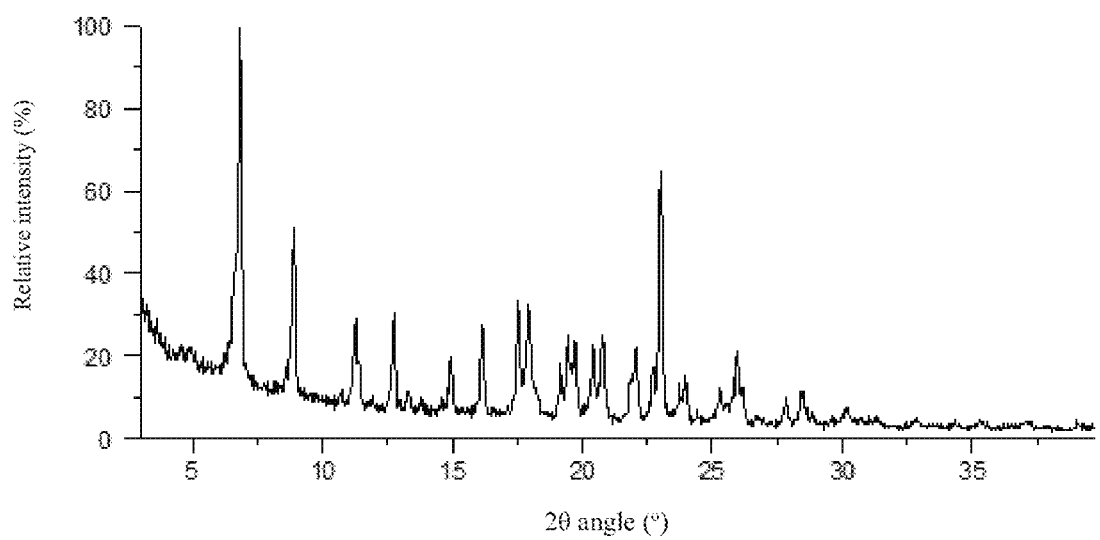
FIG. 5 is an XRPD pattern of the crystal form B of compound 1 with Cu-Kα radiation.
Figure 6:
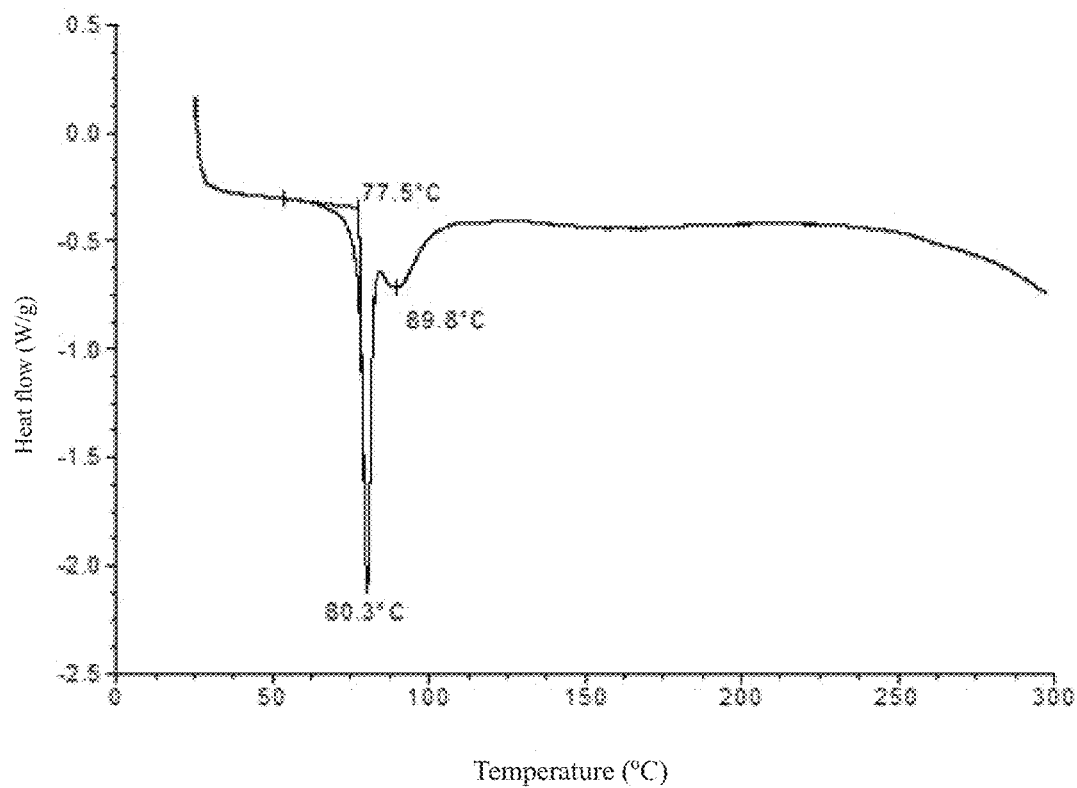
FIG. 6 is a DSC curve of the crystal form B of compound 1.
Figure 7:
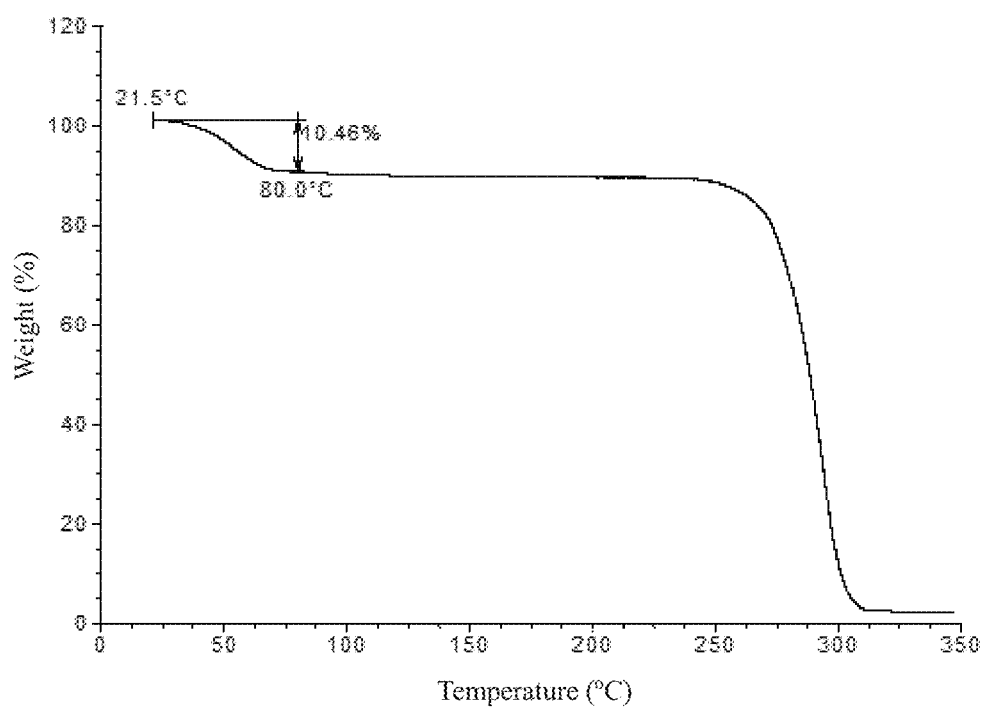
FIG. 7 is a TGA curve of the crystal form B of compound 1.

Assay Materials:
SEM Advantage-1 Dynamic Vapor Sorption Apparatus.
Assay Method:
10-30 mg of crystal form A of compound 1 was weighed and placed in a DVS sample pan for assaying.
Results of the Assay:
DVS curve of crystal form A of compound 1 was as shown in FIG. 4, ΔW=0.05%.
Conclusion:
Crystal form A of compound 1 had a hygroscopic weight gain of 0.05% at 25° C. and 80% RH, which was less than 0.2%, showing no or almost no hygroscopicity.

Assay Example 2: Stability Assay of Crystal Form A of Compound 1 in Different Solvents 17 aliquots of crystal form A of compound 1 were weighed (about 15 mg per aliquot), and an appropriate amount of a single or mixed solvent in the Table below was added, respectively. The suspension was stirred at room temperature or 50° C. for 2 weeks. Solids were collected by centrifugation, and detected by XRPD for the crystal form status. The results were shown in Table 3.

TABLE 3

Stability assay of crystal form A of compound 1 in different solvents

| No. | Solvent (volume ratio) | Temperature | Status (after 2 weeks) | Crystal form |
|---|---|---|---|---|
| 1 | Methyl tert-butyl ether | Room temperature | Suspension | A |
| 2 | Toluene | Room temperature | Suspension | A |
| 3 | Water | Room temperature | Suspension | A |
| 4 | Acetone:toluene (2:1) | Room temperature | Suspension | A |
| 5 | Ethyl acetate:m-xylene (2:1) | Room temperature | Suspension | A |

TABLE 3-continued

Stability assay of crystal form A of compound 1 in different solvents

| No. | Solvent (volume ratio) | Temperature | Status (after 2 weeks) | Crystal form |
|---|---|---|---|---|
| 6 | Acetonitrile:water (3:1) | Room temperature | Suspension | A |
| 7 | Dichloromethane:m-xylene (1:1) | Room temperature | Suspension | A |
| 8 | Isopropanol:water (98:2) | Room temperature | Suspension | A |
| 9 | Isopropanol:water (95:5) | Room temperature | Suspension | A |
| 10 | Isopropanol:water (92:8) | Room temperature | Suspension | A |
| 11 | Isopropanol:water (85:5) | Room temperature | Suspension | A |
| 12 | 2-Methyltetrahydrofuran:n-octane (4:1) | 50° C. | Suspension | A |
| 13 | Ethanol:water (3:1) | 50° C. | Suspension | A |
| 14 | 1,4-Dioxane:n-heptane (1:1) | 50° C. | Suspension | A |
| 15 | Methyl isobutyl ketone:n-hexane (2:1) | 50° C. | Suspension | A |
| 16 | 2-Butanol:m-xylene (2:1) | 50° C. | Suspension | A |
| 17 | Dimethyl sulfoxide:water (2:1) | 50° C. | Suspension | A |

Conclusion: Crystal form A of compound 1 had good stability in solvents such as methyl tert-butyl ether, toluene, water, and a mixed solvent of alcohol and water.

Assay Example 3: Solid Stability Assay of Crystal Form a of Compound 1 at High Temperature, High Humidity and Strong Light Conditions According to "Guidelines for Stability Assay of APIs and Preparations" (Chinese Pharmacopoeia 2015 Edition, Volume IV, General Principles 9001), crystal form A of compound 1 was assayed for stability at high temperature (60° C., open), high humidity (room temperature/92.5% relative humidity, open) and strong light (5000±500 Lux, 90 μw/cm², sealed).

1.5 g of crystal form A of compound 1 was weighed, placed in an open watch glass, and spread into a thin layer. The samples placed under high temperature and high humidity conditions were placed in a desiccator for inspection, and samples were taken on the $5^{th}$, $10^{th}$, and $30^{th}$ days for assaying. The assay results were compared with the initial assay results on day 0. The samples placed under strong light condition were covered with a quartz glass cover, and samples were taken on the $5^{th}$ and $10^{th}$ days for assaying. The assay results were compared with the initial assay results on day 0. The assay results were shown in Table 4 below.

TABLE 4

Results of solid stability assay of crystal form A of compound 1 under high temperature, high humidity, and strong light conditions

| Assay conditions | Sampling time point | Appearance | Content | Total impurity |
|---|---|---|---|---|
| — | Day 0 | White powder | 99.5% | 0.33% |
| High temperature (60° C., open) | Day 5 | White powder | 101.3% | 0.32% |
|  | Day 10 | White powder | 100.3% | 0.32% |
|  | Day 30 | White powder | 99.2% | 0.33% |

TABLE 4-continued

Results of solid stability assay of crystal form A of compound 1 under high temperature, high humidity, and strong light conditions

| Assay conditions | Sampling time point | Appearance | Content | Total impurity |
|---|---|---|---|---|
| High humidity (room temperature/ 92.5% relative humidity, open) | Day 5 | White powder | 101.1% | 0.32% |
|  | Day 10 | White powder | 100.3% | 0.32% |
|  | Day 30 | White powder | 99.5% | 0.33% |
| Strong light (5000 ± 500 Lux, 90 μw/cm², sealed) | Day 5 | White powder | 100.4% | 0.33% |
|  | Day 10 | White powder | 100.7% | 0.33% |

Conclusion: Crystal form A of compound 1 had good stability under high temperature, high humidity, or strong light condition.

Assay Example 4: Solid Stability Assay of Crystal Form a of Compound 1 Under Accelerated Condition According to "Guidelines for Stability Assay of APIs and Preparations" (Chinese Pharmacopoeia 2015 Edition, Volume IV, General Principles 9001), crystal form A of compound 1 was assayed for stability under accelerated condition of high temperature and high humidity (40° C./75% relative humidity, sealed).

1.5 g of crystal form A of compound 1 was weighed and placed in a double-layer low-density polyethylene bag. Each layer of low-density polyethylene bag was sealed by buckling, respectively, and then the double-layer low-density polyethylene bag was placed in an aluminum foil bag and heat-sealed. Samples were taken on the $1^{st}$, $2^{nd}$, $3^{rd}$ and $6^{th}$ months for assaying, and the assay results were compared with the initial assay results on day 0. The assay results were shown in Table 5 below.

TABLE 5

Results of solid stability assay of crystal form A of compound 1 under accelerated condition (40° C./75% relative humidity, sealed)

| Assay condition | Sampling time point | Appearance | Content | Total impurity | Crystal form (XRPD) |
|---|---|---|---|---|---|
| — | Day 0 | White powder | 99.5% | 0.33% | A |
| 40° C./75% relative humidity, sealed | Month 1 | White powder | 99.5% | 0.32% | Not detected |
| | Month 2 | White powder | 99.4% | 0.33% | Not detected |
| | Month 3 | White powder | 99.2% | 0.33% | A |
| | Month 6 | White powder | 99.5% | 0.33% | A |

Conclusion: Crystal form A of compound 1 had good stability under accelerated condition of 40° C./75% relative humidity.

Assay Example 5: Solid Stability Assay of Crystal Form A of Compound 1 Under Long-Term Condition According to "Guidelines for Stability Assay of APIs and Preparations" (Chinese Pharmacopoeia 2015 Edition, Volume IV, General Principles 9001), crystal form A of compound 1 was assayed for stability under long-term condition (25° C./60% relative humidity, sealed).

1.5 g of crystal form A of compound 1 was weighed and placed in a double-layer low-density polyethylene bag. Each layer of low-density polyethylene bag was sealed by buckling, respectively, and then the double-layer low-density polyethylene bag was placed in an aluminum foil bag and heat-sealed. Samples were taken on the $3^{rd}$ and $6^{th}$ months for assaying, and the assay results were compared with the initial assay results on day 0. The assay results were shown in Table 6 below.

TABLE 6

Results of solid stability assay of crystal form A of compound 1 under long-term condition (25° C./60% relative humidity, sealed)

| Assay Condition | Sampling time point | Appearance | Content | Total impurity | Crystal form (XRPD) |
|---|---|---|---|---|---|
| — | Day 0 | White powder | 99.5% | 0.33% | A |
| 25° C./60% relative humidity, sealed | Month 3 | White powder | 99.0% | 0.34% | A |
| | Month 6 | White powder | 99.5% | 0.33% | A |

Conclusion: Crystal form A of compound 1 had good stability under long-term condition of 25° C./60% relative humidity.

Assay Example 1: Inhibitory Activity of Compound 1 on Phosphodiesterase 4B Subtype (PDE4B Enzyme)

The biological assay was based on fluorescence polarization measurement of AMP/GMP expression, that is, tracing binding of AMP/GMP antibody to indicate the activity of the enzyme.

Agents:
Buffer solution for the assay: 10 mM trihydroxymethyl aminomethane-hydrochloric acid buffer solution (Tris-HCl) (pH 7.5), 5 mM $MgCl_2$, 0.01% polyoxyethylene lauryl ether (Brij 35), 1 mM dithiothreitol (DTT), and 1% DMSO.

Enzyme: Recombinant human PDE4B (Genebank Accession Number NM_002600; amino acid 305 terminal) was expressed with baculovirus in Sf9 insect cells using N-terminal GST tag. MW=78 kDa.

Enzyme substrate: 1 µM cAMP

Detection: Transcreener® AMP2/GMP2 antibody and AMP2/GMP2 AlexaFluor633 tracing.

Procedures:
1. Dissolving the recombinant human PDE4B enzyme and enzyme substrate (1 µM cAMP) in freshly prepared assay buffer, respectively;
2. Transferring the above PDE4B enzyme buffer solution to reaction wells;
3. Adding compound 1 dissolved with 100% DMSO to reaction wells with the PDE4B enzyme buffer solution via acoustic technology (echo 550 nanoliter range) and incubating at room temperature for 10 min;
4. Then, adding the enzyme substrate buffer solution to the above reaction wells to initiate reaction;
5. Incubating at room temperature for 1 h;
6. Adding the detection mixture (Transcreener® AMP2/GMP2 antibody and AMP2/GMP2 AlexaFluor633 tracing) to terminate the reaction and incubating with slow mixing for 90 min. The range of fluorescence polarization determination was Ex/Em=620/688.

Data Analysis:
The fluorescence polarization signal was converted into nM based on AMP/GMP standard curve and % enzyme activity calculated by Excel software relative to the DMSO control. The curve was fitted with GraphPad Prism (drawing medical icons).

TABLE 7

Results of in vitro screening assay of compound 1 disclosed herein

| Compound | $IC_{50}$ (nM)* |
|---|---|
| Compound 1 | 26.2 |

*Average in triplicate.

Conclusion:
Compound 1 exhibited excellent in vitro activity of inhibiting phosphodiesterase 4B subtype (PDE4B).

Assay Example 2: Evaluation of In Vitro Inhibition of TNFα Production in Human Peripheral Blood Mononuclear Cells (hPBMC)

Purpose of the Assay:
Inhibitory activity of compound 1 on lipopolysaccharide (LPS)-induced TNFα production in human peripheral blood mononuclear cells.

Procedures:
1. PBMC Assay
PBMC cells were inoculated into a 96-well plate of cell culture grade at a density of 100,000 cells/100 µL/well. The cell culture medium was RPMI-1640 supplemented with 10% serum. The plate was incubated in a 37° C., 5% $CO_2$ incubator for 2 hours. 16.8 µL/well of the assay compound was added to the cells and then the cells were incubated in a 37° C., 5% $CO_2$ incubator for 60 minutes. 16.8 µL/well of LPS was then added to the cells and the cells were incubated in a 37° C., 5% $CO_2$ incubator for 18 hours. The final DMSO concentration was 0.1%.

2. Gradient Dilution of Dose of Compound

In the first step, compound 1 was diluted from a stock concentration to 1.5 mM with 100% DMSO. In the second step, the diluted compound was used as the first point and serially diluted 3-fold with 100% DMSO for 9 points. In the third step, the compound was diluted 125-fold with a serum-free medium, at which time the concentration of DMSO was 0.8%. Then 16.8 μL of the compound diluted with the medium was transferred to a 100 μL cell plate.

The compound was added, and then the cell plate was placed in a 37° C., 5% $CO_2$ incubator and incubated for 1 hour.

3. Dilution of LPS

In the first step, LPS was diluted with ultrapure water to a stock concentration of 1 mg/mL. In the second step, the LPS with a stock concentration was diluted with a serum-free medium to 1 μg/mL. In the third step, the LPS was diluted 1666.666-fold with a serum-free medium. Then 16.8 μL of LPS diluted with the medium was transferred to 116.8 μL cell plate, at which time the final concentration of DMSO was 0.1%. LPS was added, and then the cell plate was placed in a 37° C., 5% $CO_2$ incubator and incubated for 18 hours.

4. ELISA Assay

1) TNF-α antibody was diluted in a coating solution to 1 times volume, and then added to a 96-well plate with high binding performance at 100 μL per well. The plate was sealed with a membrane and placed in a refrigerator at 4° C. for 18 hours.
2) 2000 mL of wash buffer was formulated to 1 times volume for use.
3) After the plate was coated overnight, the coating solution was poured out and the plate was washed 3 times with 300 μL of wash buffer per well.
4) After washing the plate, 200 μL of blocking buffer was added to each well, and the plate was sealed with a membrane. The plate was placed in an incubator at 25° C. and incubated for one hour.
5) The cell plate incubated for 18 hours was centrifuged in a centrifuge (temperature: 25° C., rotation speed: 2000 rpm, time: 10 minutes, speed increase: 9, speed decrease: 1). After centrifugation, 100 μL of cell supernatant per well was transferred to a 3599 cell plate, and the plate was then placed in a refrigerator at 4° C. for use.
6) The cell supernatant was diluted 40-fold with blocking buffer and placed in a refrigerator at 4° C. for use. Standard was formulated and also placed in a refrigerator at 4° C. for use.
7) After the blocking was completed, the blocking solution was poured out, and the plate was washed 3 times with 300 μL of wash buffer per well.
8) The diluted cell supernatant samples and standards were added to a ELISA plate. The plate was sealed with a membrane, and then placed in an incubator at 25° C. and incubated for two hours.
9) The liquid in the plate was poured out, and the plate was washed 5 times with 300 μL of wash buffer per well.
10) Antibody was prepared, and added to the plate at 100 μL/well. The plate was sealed with a sealing membrane, and then placed in an incubator at 25° C. and incubated for one hour.
11) The liquid in the plate was poured out, and the plate was washed 7 times with 300 μL of wash buffer per well.
12) Chromogenic solution was prepared, and added to the plate at 100 μL/well. The plate was then placed in an incubator at 25° C. and incubated in the dark for half an hour.
13) 50 μL of stop solution was added to each well, and the plate was then centrifuged (temperature: 25° C., rotation speed: 1000 rpm, time: 1 minute, speed increase: 9, speed decrease: 9).
14) The plate was read on Envision within 30 minutes after centrifugation, and a value obtained by subtracting the absorbance at 570 nm from the absorbance at 450 nm was set as the final original data for use.

5. Data Processing

Inhibition rate was calculated based on original data according to the formula of:

Inhibition rate=(1−(original value−HPE average)/ (ZPE average−HPE average))*100 wherein ZPE is: 0% inhibition (75 pg/mL LPS, 0.1% DMSO), and HPE is: 100% inhibition (without LPS, 0.1% DMSO).

Data analysis was performed with XLfit statistical software. IC50 was calculated by the following method: the concentration and the inhibition rate (%) of the assayed compound was plotted using a 4-parameter logistic dose-response equation, and the compound concentration required for 50% inhibition (IC50) was determined.

TABLE 8

Results of inhibitory activity of compound 1 disclosed herein on TNFα production in hPBMC

| Compound | $IC_{50}$ (nM)* |
|---|---|
| Compound 1 | 63.92 |

*Average in triplicate.

Conclusion:

Compound 1 exhibited excellent in vitro activity of inhibiting TNFα production in hPBMC.

Assay Example 3: In Vivo Model of PMA-Induced Ear Edema in CD-1 Mice

Purpose of the Assay:

Inflammatory edema, also known as tissue edema, is edema caused by accumulation of exudate caused by inflammation in interstices of tissues. An obvious inflammatory response mediated by protein kinase C (PKC) can be caused when administered topically to ears of mice with phorbol 12-myristate 13-acetate (PMA), thereby triggering a series of symptoms similar to human atopic dermatitis (AD). In the process of preclinical evaluation of candidate compounds for the treatment of AD, an animal model of PMA-induced ear edema in mice is usually used to evaluate the effectiveness.

The purpose of this assay was to investigate the therapeutic effect of compound 1 on the model of PMA-induced ear edema in CD-1 mice, so as to provide preclinical pharmacodynamic information for subsequent clinical studies.

Assay Method:
1. Preparation of PMA 1 mL of acetone was added to completely dissolve 1 mg of PMA, and then 800 μL of mother liquor was pipetted and added to 2400 μL of acetone to prepare 0.25 mg/mL PMA.

2. Induction by PMA

CD-1 mice were sorted according to ear thickness and body weight. After removing four mice that were significantly different from the mean, the remaining mice were randomly divided into a normal control group including 6 mice and treatment groups (10 mice in each treatment group). 10 μL of PMA with a concentration of 0.25 mg/mL was applied to the front and back sides of the right ear of each mouse.

The induction did not need to be performed on mice in the normal control group.

3. Administration and Dosage Design

The mice in the first group were normal mice, and these mice will not be treated in any way; the mice in the second group were given a vehicle; and the mice in the third group, the fourth group, and the fifth group were given compound 1 at a dose of 0.1 mg/ear, 0.3 mg/ear, and 1 mg/ear, respectively. Drugs were applied to the right ear of the mice 30 minutes before and 15 minutes after PMA induction, respectively.

TABLE 9

Grouping and dosage design in the assay

| Groups | Assay drug | Quantity | Route of administration | Dosage mg/ear | Frequency of administration |
|---|---|---|---|---|---|
| G1 | Normal group | 6 | NA | NA | NA |
| G2 | Vehicle group | 10 | Application | NA | BID |
| G3 | Compound 1 | 10 | Application | 0.1 | BID |
| G4 | Compound 1 | 10 | Application | 0.3 | BID |
| G5 | Compound 1 | 10 | Application | 1 | BID |

Note:
NA represents "not available"; and BID represents "dosing twice a day".

4. Determination of Incidence Index of Ear Edema

Measurement and sampling: Ten hours after PMA induction, the mice were anesthetized and the thickness of the right ear was measured. After measuring the thickness of the right ear, the mouse was immediately euthanized, and the ear piece was collected and weighed.

5. Statistical Processing

The assay data was expressed as mean±standard error of mean (Mean±SEM), and the degree of ear swelling and ear weight were analyzed by one-way analysis of variance (One-way ANOVA), wherein p<0.05 was considered a significant difference.

Results of the Assay:

By measuring at the time point of 10 hours after PMA induction, the ear thickness increased by 0.300-0.400 mm, which was much higher than the normal swelling range (−0.010 to 0.002 mm), and the ear weight increased by 28.8 mg on average, indicating that the ear edema model was established successfully.

Assay compound 1 can significantly reduce the edema degree of ear edema mice at the 10-hour point at three doses of 0.1 mg/ear, 0.3 mg/ear, and 1 mg/ear, and showed a good dose-effect relationship, wherein the inhibition rates of ear edema were 22%, 39%, and 88%, respectively, and the inhibition rates of ear weight gain were 39%, 46%, and 85%, respectively (compared with the vehicle control group, all p values were less than 0.0001).

Conclusion:

In the three dose groups of 0.1, 0.3 and 1 mg/ear, compound 1 had a significant improvement effect on the symptoms of PMA-induced ear edema, can significantly inhibit ear weight gain, and showed a good dose-effect relationship in all the three dose groups.

What is claimed is:

1. A crystal form A of compound 1, which has an X-ray powder diffraction pattern comprising characteristic diffraction peaks at 2θ angles of: 11.26±0.20°, 11.91±0.20°, 12.91±0.20°, 14.27±0.20°, 15.83±0.20°, 19.36±0.20°, 20.33±0.20°, 22.26±0.20°, 23.17±0.20°, and 24.97±0.20°

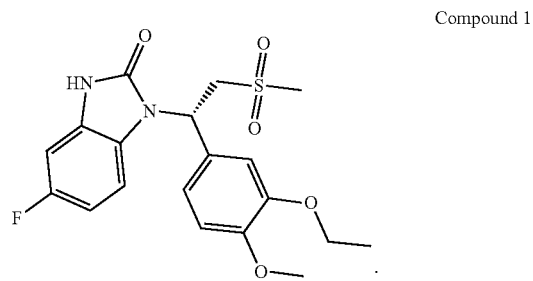 [SMILES: CCOc1cc([C@@H](CS(C)(=O)=O)n2c(=O)[nH]c3cc(F)ccc32)ccc1OC]

Compound 1

2. The crystal form A of compound 1 according to claim 1, wherein the X-ray powder diffraction pattern comprises characteristic diffraction peaks at 2θ angles of: 11.26±0.20°, 11.91±0.20°, 12.91±0.20°, 14.27±0.20°, 15.83±0.20°, 17.53±0.20°, 19.36±0.20°, 20.33±0.20°, 22.26±0.20°, 23.17±0.20°, 24.97±0.20°, and 26.50=0.20°.

3. The crystal form A of compound 1 according to claim 2, wherein the X-ray powder diffraction pattern comprises characteristic diffraction peaks at 2θ angles of: 11.26°, 11.91°, 12.91°, 14.27°, 15.83°, 17.53°, 19.36°, 20.33°, 22.26°, 22.59°, 23.17°, 24.97°, 26.50°, and 29.46°.

4. The crystal form A of compound 1 according to claim 3, wherein the XRPD pattern is as shown in FIG. 1.

5. The crystal form A of compound 1 according to claim 1, which has a differential scanning calorimetry curve having an onset of an endothermic peak at 147.0±3.0° C.

6. The crystal form A of compound 1 according to claim 1, which has a thermogravimetric analysis curve having a weight loss of up to 0.70% at 140.0±3.0° C.

7. A method of reducing TNFα production in a subject having an inflammatory disease, the method comprising administering to the subject the crystal form A of compound 1 according to claim 1, wherein the disease is an inflammatory disease.

* * * * *